United States Patent [19]

Trujillo et al.

[11] Patent Number: 5,702,949
[45] Date of Patent: Dec. 30, 1997

[54] CULTURE METHOD FOR MULTILAYER GROWTH OF ANCHORAGE-DEPENDENT CELLS

[75] Inventors: Edward M. Trujillo, Sandy; Catherine Rappaport, Salt Lake City, both of Utah

[73] Assignee: University of Utah Research Foundation, Salt Lake City, Utah

[21] Appl. No.: 665,822

[22] Filed: Jun. 19, 1996

Related U.S. Application Data

[60] Provisional application No. 60/004,089, Jun. 22, 1995.
[51] Int. Cl.$^6$ .................................................. C12N 5/00
[52] U.S. Cl. ................................................ 435/402; 435/395
[58] Field of Search ........................................ 435/395, 402

[56] References Cited

U.S. PATENT DOCUMENTS

| | | | |
|---|---|---|---|
| 3,997,396 | 12/1976 | Delente | 435/400 |
| 4,954,444 | 9/1990 | Eveleigh et al. | 435/181 |
| 5,010,009 | 4/1991 | Steele et al. | 435/402 |
| 5,037,656 | 8/1991 | Pitt et al. | 424/443 |
| 5,077,215 | 12/1991 | McAuslan et al. | 435/423 |
| 5,180,676 | 1/1993 | Ichikawa et al. | 435/383 |
| 5,243,037 | 9/1993 | Arentzen et al. | 536/18.4 |
| 5,246,451 | 9/1993 | Trescony et al. | 623/1 |
| 5,342,772 | 8/1994 | Arenzen et al. | 435/181 |
| 5,384,254 | 1/1995 | Arentzen et al. | 435/181 |
| 5,491,083 | 2/1996 | Arentzen et al. | 435/181 |

OTHER PUBLICATIONS

"Behavior of Cells at Fluid Interfaces", Ivar Giaever and Charles R. Keese, *Proc. Natl. Acad. Sci. USA*, vol. 80, Jan. 1983, pp. 219–222.

"Cell Growth on Liquid Microcarriers", Charles R. Keese and Ivar Giaever, *Science*, vol. 219, 24 Mar. 1983, pp. 1448–1449.

"Perfluorochemicals in Biotechnology", Bo Mattiasson and Patrick Adlercreutz, *Tibtech*, vol. 5, Sep. 1987, pp. 250–254.

"Growth of Cells on a Perfluorocarbon–Medium Interphase: A Quantitative Assay for Anchorage–Independent Cell Growth", Brunella Sanfilippo, Fortunato Ciardiello, David S. Salomon, and William R. Kidwell, *In Vitro Cellular & Developmental Biology*, vol. 24, No. 1, Jan. 1988, pp. 71–78.

"Perfluorochemicals and Cell Culture", Alastair T. King, Bernard J. Mulligan, and Kenneth C. Lowe, *Bio/Technology*, vol. 7, Oct. 1989, pp. 1037–1042.

"Artificial Organs from Culture", Jennifer Van Brunt, *Bio/Technology*, vol. 9, Feb. 1991, pp. 136–137.

"Culture of Human Adult Endothelial cells on Liquid–Liquid Interfaces: A New Approach to the Study of Cell–Matrix Interactions", Joji Ando, Steven M. Albelda, and Elliot M. Levine, *In Vitro Cellular & Developmental Biology*, Jul. 1991, pp. 525–532.

"Enhancing Oxygen Transfer in Bioreactors by Perfluorocarbon Emulsions", Lu–Kwang Ju, Jaw Fang Lee, and William B. Armiger, *Biotechnology Prog.*, 1991, pp. 323–329.

"Microelectrode measurements of Pericellular Po$_2$ in Erythropoietin–Producing Human Hepatoma Cell Cultures", Wolff et al., *The American Physiological Society*, 1993, pp. C1266–C1270.

(List continued on next page.)

*Primary Examiner*—George C. Elliott
*Assistant Examiner*—Johnny F. Railey, II
*Attorney, Agent, or Firm*—Madson & Metcalf

[57] ABSTRACT

Anchorage-dependent cells are grown on a novel substratum which is believed to increase the oxygenation of the cells and reduce the formation of free-radicals. The substratum consists of a perfluorocarbon reservoir which is coated with a layer of protein (e.g., collagen or gelatin) which has been perfluoroalkylated. The perfluoroalkylated protein forms a very stable surface to which anchorage-dependent cells can attach and grow. Using this system, mammalian cell cultures have been grown to densities exceeding $10^7$ cells/cm$^2$. The increased density is attributed to the formation of multiple cell layers which resemble tissue-like structures.

19 Claims, 6 Drawing Sheets

OTHER PUBLICATIONS

"Oxygen Uptake Rates in Cultured Rat Hepatocytes", Rotem et al., *Biotechnology and Bioengineering*, 1992, vol. 40, pp. 1286–1291.

"Immobilization of Perfluoroalkylated Enzymes in a Biologically Active State onto Perflex Support", Biovin et al., *Biotechnology and Applied Biochemistry*, 1991, vol. 14, pp. 155–169.

"Diffusion in Tissue Cultures on Gas-Permeable and Impermeable Supports", Wallach et al., *J. Ther. Biol.*, 1976, vol. 56, p. 443–458.

CULTURE METHOD FOR MULTILAYER GROWTH OF ANCHORAGE-DEPENDENT CELLS

RELATED APPLICATIONS

This application claims the benefit of U.S. provisional application Ser. No. 60/004,089, filed Jun. 22, 1995 of Edward M. Trujillo and Catherine Rappaport, and entitled "Perfluorocarbon Coupled Perfluoroalkylated Substrates and Method for Improving Oxygenation of Aqueous Culture Media" which provisional application is incorporated herein by this reference.

1. The Field of the Invention

The present invention is related to a system for cultivating cells. More specifically, the present invention is related to a novel oxygenation system which supports multilayer growth of anchorage-dependent cells. In one embodiment, this is accomplished by seeding the cells on a perfluoroalkylated protein/perfluorocarbon surface to which anchorage-dependent cells can attach and grow to previously unattainable densities and cell layers.

2. Technical Background

Cell cultures are cells from a plant or animal which are grown outside the organism from which they originate. These cells are often grown, for example, in petri dishes under specific environmental conditions. Cell cultures are of great importance because they represent biological "factories" capable of producing large quantities of bioproducts such as growth factors, antibodies and viruses. These products can then be isolated from the cell cultures and used, for example, to treat human disease. In addition, tissue cultures are a potential source of tissues and organs which could be used for transplantation into humans. For example, tissue cultured skin cells could potentially be used in skin grafts. Finally, tissue cultures usually comprise cells from only one or a few tissues or organs. Consequently, cell cultures provide scientists a system for studying the properties of individual cell types without the complications of working with the entire organism.

In vivo, cells form complex multilayer structures which ultimately form tissues and organs. These cells receive their nutrient and oxygen requirements via the blood in the circulatory system. In addition, in order to form tissues and organs, cells must form contacts with each other and with an extracellular matrix. Extracellular matrices comprise a complex and variable array of collagens, glycosaminoglycans, proteoglycans, and glycoproteins. Together these cellular products form the basal lamina, bone, and cartilage which give tissues and organs their shape and strength. The contact between anchorage-dependent cells and the extracellular matrix plays a dramatic role in determining the cells' shape, position, metabolism, differentiation and growth.

Like most cells in vivo, many cells are anchorage-dependent; that is, they can metabolize and divide only if they are attached to a surface or substratum. Only cells of the circulatory system (e.g., lymphocytes and red blood cells) grow unattached and suspended in solution in vitro. While many anchorage-dependent cells may grow on glass or plastic surfaces, these cells often lose their ability to differentiate and respond to hormones. For this reason, glass and plastic tissue culture dishes are often coated with an extracellular matrix such as collagen.

Unlike cells in vivo, normal cells in culture do not form significant multilayer structures. Under optimal conditions, for example, epithelial cells grow only one cell layer thick (monolayer), while fibroblast cells at best grow two or three layers thick. Once the growing surface is confluent with cells, normal cells cease to divide and their number actually begins to decline with time. This phenomenon is referred to as "density-dependent inhibition."

The failure of cells to grow to form multilayered structures is a major limitation of current tissue culture techniques. Cells growing in monolayers often lose the capacity to perform many essential functions that they perform in their respective tissues and organs. This is primarily due to the fact that in vivo these cells are surrounded by other cells which provide many factors needed for normal function and growth. Thus, current research is hindered by the fact that tissue culture techniques do not accurately mimic in vivo biological activity.

It is believed that the inability of cells in culture to form multilayer structures is owed, in part, to lack of oxygenation. Oxygen, unlike other nutrients, is only sparingly soluble in aqueous media. Thus, cells several cell layers deep do not receive sufficient oxygen to grow and maintain normal biological activity. Conventionally, two methods have been used to improve oxygenation for cell growth in bioprocesses: mechanical stirring and bubbling. Cultures have been mechanically stirred to increase oxygen transport at the aqueous/air interface and distribute oxygen uniformly in the culture fluid. This results in shear and other problems with anchorage-dependent mammalian cells which lack a rigid cell wall and are large (10–100 µm) and very fragile. Also, anchorage-dependent mammalian cells cannot rotate or translate freely to reduce the net forces and torques from shear because they are attached and fixed to the substratum. Studies suggest that the viability of endothelial and human kidney cells is profoundly affected by shear. These effects are observed at shear rates as low as 1 dyne/cm$^2$. Cell shear stress is also created when air bubbles contact the cell or bioparticle. Typically, higher bubbling flow rates per unit volume increase the specific death rate of anchorage-dependent mammalian cells in microcarrier systems.

Shear stress may also cause changes in the shape and function of cells. If the stress is strong enough, anchorage-dependent cells can be detached from the surface to which they are attached. In addition, some cell functions, such as cytoskeleton assembly, metabolism, biomolecular synthesis, are also shear stress dependent, even under conditions of laminar flow.

Many investigators have added a polymer to the medium to reduce hydrodynamic effects. This has been found to provide some protection. The most frequently used polymers are methylcellulose, polysucrose, Dextran, and Pluronic F-68. It is believed that the polymers adhere to the cell surface and form a protective shell against shear and mechanical forces. However, whether a protective shell is actually formed or the effects it may have on normal cell function is unknown.

Another method for increasing oxygenation to cell cultures is the hollow fiber membrane bioreactor. In this system, the cells are attached to a cylindrical hollow fiber membrane. Culture media and oxygen flows through the center of the cylindrical hollow fiber membrane. The molecular weight cut-off of the membrane permits nutrients and oxygen to reach the cells without allowing the cells to escape. However, the formation of multilayer of cells was not observed.

Apart from the problem of poor oxygenation, current tissue culture techniques produce free radicals. Free radicals are atoms or polyatomic molecules which posses one unpaired electron. In culture media, free radicals arise from the reaction of oxygen with iron, or copper, as well as certain metabolites which are normally present in growth media. Studies have shown that free radicals are toxic to mammalian cells, even at very low levels. Thus, benefits derived from increased oxygenation of culture media using molecular oxygen, would likely be countered by increased free radicals.

More recently, perfluorocarbons (PFCs) have been used to increase oxygenation of cultures. Perfluorocarbons are organic compounds where all hydrogen atoms are replaced by fluorine atoms. Oxygen is 15 to 20 times more soluble in PFCs that in water. As a result, PFCs are sometimes referred to as "psuedoerythrocytes" because they are oxygen-carrying molecules analogous to the erythrocytes that carry oxygen in mammalian blood. Indeed, PFCs have been used as oxygen carriers in place of red blood cells in animals.

Current tissue culture techniques which employ PFCs, however, have their own limitations. One method teaches continuously adding an oxygenated PFC to the top of the culture media. The PFC being denser than the aqueous culture media sinks to the bottom of the bioreactor where it is removed. While this system successfully improved the oxygenation of the culture media, it has two significant disadvantages. First, the system is limited to suspension cells which must be mechanically stirred in order to prevent them from settling at the bottom of the reactor. As discussed above, this damages mammalian cells. Second, the PFC comes into direct contact with the cells. PFC has been shown to alter the normal biological activity of various cells in culture. For example, neutrophils and monocytes incubated with PFCs exhibit decreased phagocytic activity, chemotaxis, aggregation, cellular adherence, and superoxide ion release.

Currently, cultivation of anchorage-dependent mammalian cells using PFCs has been unsuccessful. The principal difficulty is that anchorage-dependent mammalian cells do not adhere to PFC surfaces or do not adhere any better than on conventional polystyrene surfaces. A few studies have reported some growth on microspheres (diameter 100 to 500 µm) made by emulsifying perfluorotertiary amine. It was found, however, that the cells were actually growing on a layer of protein desorbed from the serum used in the nutrient medium. This layer was not stable and growth was erratic. Moreover, the cultures had to be vigorously stirred to ensure equilibration with oxygen resulting in cellular damage. Finally, since serum contains very little extracellular matrix material, the microspheres did not provide a good substratum for anchorage-dependent cell growth. In fact, growth on these microspheres was not as good as on commercially available microcarriers fabricated with collagen, or gelatin.

From the foregoing, it will be appreciated that it would be an advancement in the art to provide a system which provides improved oxygenation to anchorage-dependent tissue culture cells.

It would be a further advancement in the art if the anchorage-dependent tissue were able to form multilayer tissue-like structures.

It would be yet another advancement in the art if the improved oxygenation could be accomplished without mechanically stirring or agitating the culture media.

It would also be an advancement in the art if the increased oxygenation resulted from perfluorocarbon molecules that were not in direct contact with the tissue culture cells.

Finally, it would be an advancement in the art if the amount of free radicals produced in the culture media were greatly reduced or eliminated.

Such a system is disclosed and claimed herein.

BRIEF SUMMARY OF THE INVENTION

The present invention is directed to a novel oxygenation system which supports multilayer growth of anchorage-dependent cells. More particularly, the invention relates to a substratum for growing culture cells in vitro which is capable of forming 3-dimensional tissue-like structures. The substratum consists of a reservoir of oxygenated perfluorocarbon (PFC). The surface of the PFC reservoir is coated with a layer of an extracellular matrix protein, or other protein to which culture cells can attach, which has been perfluoroalkylated. Perfluoroalkylated chemically bonds a PFC tail to the extracellular matrix protein. The PFC tail of the protein can then bind with the PFC reservoir, anchoring the protein and creating a strong, stable surface on which anchorage-dependent culture cells can attach and grow.

This novel tissue culture technique overcomes several problems facing the art. First, the perfluoroalkylated protein/perfluorocarbon (PF-protein/PFC) substratum of the present invention is capable of continually supplying high concentrations of oxygen to the culture cells. The high affinity of PFC for oxygen permits high concentrations of oxygen to pass through the PF-protein interface and reach the culture cells. No mechanical stirring or agitation is required. Depending on the intended use, the PFC reservoir can either be a closed system with a finite supply of oxygen or an open system which is continuously regenerated with oxygen.

In one preferred embodiment, HeLa cells were seeded on perfluoroalkylated gelatin (PF-gelatin) which was anchored to an open system perfluorodecalin (PFD) reservoir. After 15 days, the cells had reached a density of $1.1 \times 10^7$ cells/cm$^2$. More importantly, a 3 micron vertical section stained with hematoxylin and eosin showed that cells had grown to form more than 19 layers. Mitotic figures deep within the multilayer demonstrate that the cells were receiving enough oxygen in order to divide.

Second, the system of the present invention limits free radicals. As discussed above, free radicals are toxic to mammalian cells at even very low concentrations. PFCs do not contain free radicals. Moreover, the PFC which delivers oxygen to the cells never comes in direct contact with the growth media. The PFC and the aqueous growth media are separated by the PF-protein interface and at least one layer of cells. Thus, the oxygen is not as available for reaction with the iron, copper and other metabolites in the growth media which produce free radicals.

Finally, the PFC is never in direct contact with cells. As discussed above, PFCs have been shown to adversely affect cells in culture. In the system of the present invention, the PFC reservoir is separated from the cells by the PF-protein interface which the cells grow on. Thus, the harmful effects of PFCs on cells is greatly reduced.

Taken together, the increased oxygenation, reduced free radicals, and reduced exposure to PFCs, has resulted in a novel system for growing cells which yields three dimensional tissue-like structures never before achieved in culture. These and other objectives and advantages of the present invention will become apparent by examination of the following description of the accompanying drawings, the detailed description of the invention and the appended claims.

SUMMARY OF THE DRAWINGS

A more particular description of the invention briefly described above will be rendered by reference to the appended drawings and graphs. These drawings and graphs only provide information concerning typical embodiments of the invention and are not therefore to be considered limiting of its scope.

DETAILED DESCRIPTION OF THE INVENTION

Figures 1, 1A:
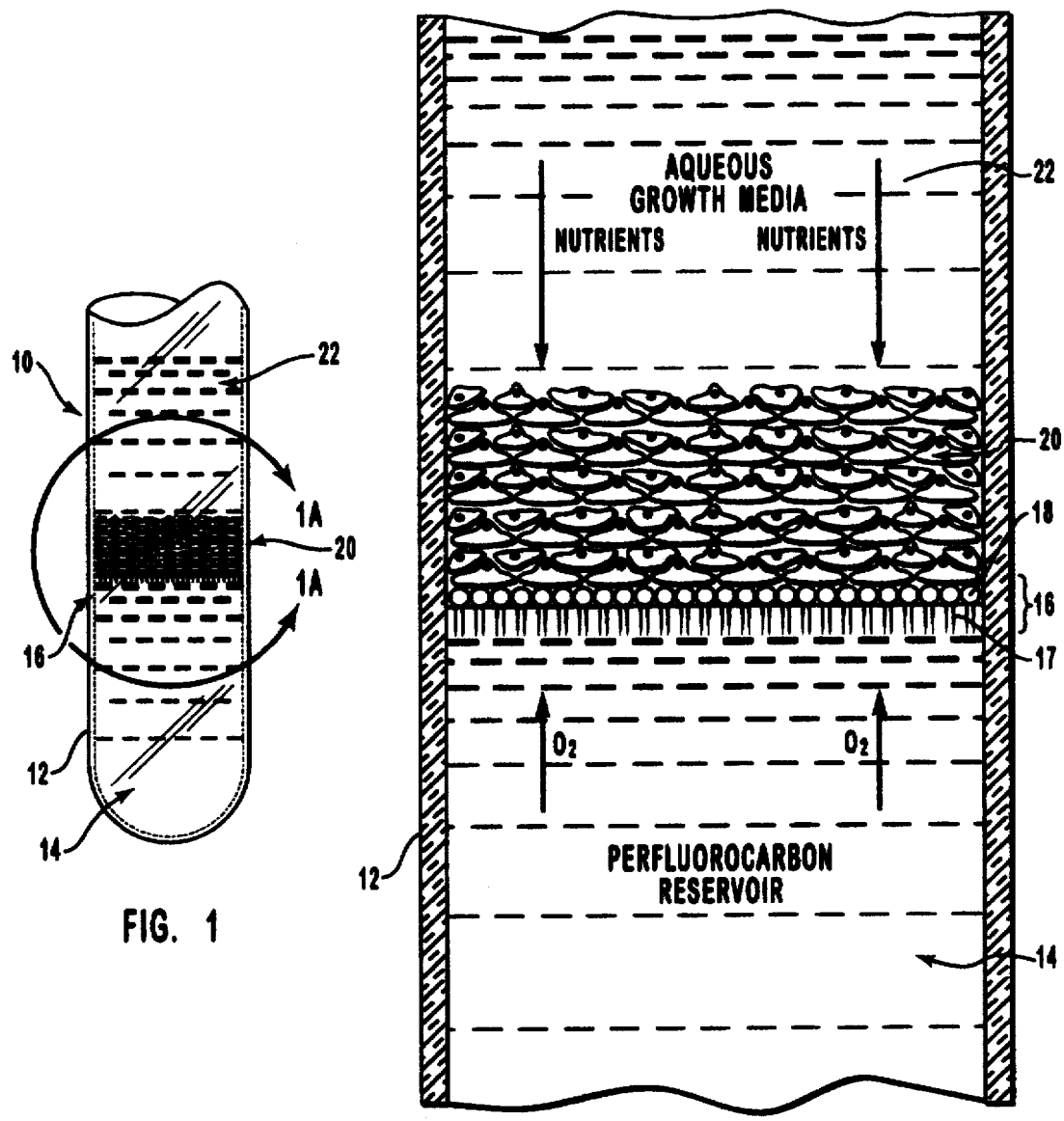
FIG. 1 is a cross sectional view of one embodiment of the present invention illustrating cells grown on a perfluoroalkylated-gelatin/perfluorodecalin substratum in a test tube.
FIG. 1A is an expanded view of the perfluoroalkylated-gelatin/perfluorodecalin—cell interface of FIG. 1.

The present invention is directed to a novel oxygenation system which supports growth of anchorage-dependent cells. This is achieved using a substratum capable of supporting 3-dimensional tissue-like structures. Reference is now made to the figures wherein like parts are referred to by like numerals. With reference to FIG. 1, in one preferred embodiment, the present invention is a system 10 for multilayer growth of anchorage-dependent cells 20. The system 10 comprises a test tube 12, a perfluorocarbon (PFC) reservoir 14, a PF-protein/PFC substratum 16 and aqueous growth media 22. The system is constructed by first adding an appropriate amount of oxygenated PFC to the bottom of a sterile test tube 12 or other container, thus forming a PFC-reservoir 14. On the surface of the PFC reservoir 14 a PF-protein/PFC substratum 16 is formed. Aqueous growth media 22 is then layered over the PF-protein/PFC substratum 16. Finally, anchorage-dependent cells 20 are added to the growth media 22 where they settle to the PF-protein/PFC substratum 16, attach and grow.

With reference to FIG. 1A, the PF-protein/PFC substratum 16 comprises a protein 18, such as gelatin or other protein to which culture cells can attach, which has been perfluoroalkylated. Perfluoroalkylation substitutes one of the hydrogens of a free amino group of the protein 18 with a PFC tail 17. With continued reference to FIG. 1A, the PFC tail 17 of the protein 18 binds with the PFC reservoir 14, anchoring the protein 18 and creating a strong stable surface. Once the PFC tail 17 binds to the PFC reservoir 14, conventional aqueous growth media 22 is supplied and anchorage-dependent culture cells 20 are seeded on the PF-protein/PFC substratum 16. The anchorage-dependent culture cells 20 are finally overlayed with conventional aqueous growth media 22. Thus, the oxygen required for cell viability and growth is supplied both by the PFC reservoir 14 which is underneath the anchorage-dependent culture cells 20 and the aqueous growth media 22 which is above the cells. Nutrients and growth factors are supplied by the aqueous growth media 22 which is above the anchorage-dependent culture cells 20.

To better understand the details of the invention, the discussion of the invention below is divided into three parts: the perfluorocarbon (PFC) reservoir, the PFC-protein/PFC substratum and cell growth.

Perfluorocarbon Reservoir

In the present invention, the PFC reservoir delivers high concentrations of oxygen to the tissue culture cells. Perfluorocarbons are organic compounds where all hydrogen atoms are replaced by fluorine atoms. The carbon-fluorine bond of perfluorocarbons is so strong (116 kcal/mol, compared with C-H, 80.36 kcal/mol) that they are very stable and inert for biological processes. Importantly, PFCs do not produce free radicals.

Perfluorocarbons are also quite apolar compounds. Since the solubility of gases increases as the polarity of the solvent decreases, PFCs are useful gas transferring molecules. For example, oxygen is 15 to 20 times more soluble in PFC than water. As a result, PFCs are of great interest in tissue culture. Other properties of PFC molecules are well documented in patents and scientific articles, including King, A. T., B. J. Mulligan and K. C. Lows, "Perfluorochemicals and Cell Culture," Bio/Technol., 7(10), 1037–1042 (1989) and Faithful, N. S., "Second Generation Fluorocarbons," Adv. Exp. Med. Biol. 317:441–52 (1992) which are hereby incorporated by reference.

The structure of some PFCs is shown below:

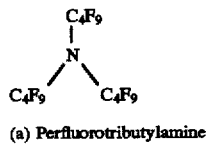

(a) Perfluorotributylamine

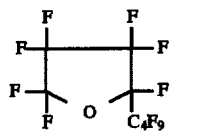

(b) Perfluorobutyltetrahydrofuran

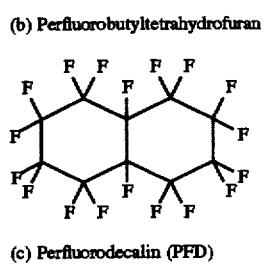

(c) Perfluorodecalin (PFD)

Other PFCs which would be useful in the present invention include fluorinated liquids manufactured by Minnesota Mining and Manufacturing Company (3M). It is understood by one skilled in the art that this list is not exhaustive but merely representative of the types of PFC molecules that fall within the scope of this invention.

PF-protein/PFC Substratum

Protein

Most mammalian cells are anchorage-dependent. Therefore, attachment to a compatible substratum is necessary for growth. This approximates in vivo environmental conditions where cells grow as a continuum, attached to other cells or to basal membranes by the extracellular matrix (ECM). A special protein (called transmembrane linker protein) binds to a cell surface receptor (called intracellular attachment protein) and then interacts with the extracellular matrix so that the cell attaches to the matrix.

One of the most important compounds in ECMs is collagen. Collagens are abundant in mammals, constituting about 25 weight percentage of the total protein. As many as 15 different types of collagens have been identified. The first four types, labeled I, II, III and IV, have been used for attachment and growth. Types I, II and III are the most abundant and form fibrils and the linear structure. Type IV is a two-dimensional sheetlike structure and forms the two-dimensional reticulum in ECM. It is well known and documented in the prior art that different types of cells adhere to certain types of collagen.

Gelatins are denatured collagens. The natural conformation of the collagen is stabilized by several types of interactions, principally hydrogen bonding. This conformation can be destroyed and denatured by heating or by alkaline treatment. Heating collagens, generally at 60°–65° C., causes the helices to unravel. On cooling the triple-helical conformations are regenerated to some extent. However, these reconfirmations are not exactly like the original collagens and are called gelatins. Anchorage-dependent cells also adhere well to surfaces treated with gelatin.

The present invention is not limited to collagen or gelatin. Other important proteins in the extracellular matrix to which cells attach are expected to fall within the scope of the present invention. These include, but are not limited to, fibronectins, laminins and elastins. Fibronectins and laminins are substrate adhesion molecules (SAM) which help cells bind to the extracellular matrix. Elastins are cross-linked random coils, insoluble proteins that give tissue its elasticity, and are the main components of elastic fibers.

Perfluoroalkylation

Overlaying an extracellular protein directly on the PFC reservoir would not provide a stable enough surface for the attachment and growth of anchorage-dependent cells. Therefore, in one preferred embodiment the protein is perfluoroalkylated. The technique involves using a perfluoroalkylating agent to chemically bind a PFC to a protein. This provides a hydrophobic perfluorocarbon tail which sinks into the PFC reservoir surface, thus firmly anchoring the protein to the PFC reservoir. The general perfluoroalkylation reaction is:

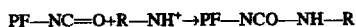

where $PF-NC=O$ is the perfluoroalkylating agent and $R-NH$ represents an amino group in the protein. Because the isocyanate group reacts with water, the reaction must be carried out in a moisture-free environment. In one preferred embodiment, gelatin was perfluoroalkylated with perfluorooctylpropyl isocyanate ($C_8F_{17}(CH_2)_3NCO$). However, other perfluoroalkylating agents with alkyl groups of varying lengths or ring structures could be used to perfluoroalkylate proteins.

After the reaction, the efficiency of the reaction is determined using a fluorescamine assay. Briefly, the perfluoroalkylated protein is reacted with fluorescamine which readily reacts with free amino groups. The fluorescence of the molecule is then measured at 350 nm. The efficiency of perfluoroalkylation varies with different proteins. This is due to a difference in number and accessibility of the amino groups. For example, gelatin is perfluoroalkylated poorly compared to bovine serum albumin (BSA). Therefore, the efficiency of perfluoroalkylation should be determined for each protein used to insure that the protein is adequately perfluoroalkylated.

PF-protein/PFC Interface

Once the desired protein is perfluoroalkylated, it must be bonded to the surface of the PFC reservoir. Enough PF-protein is added to each test tube to completely cover the top surface of the PFC reservoir. As illustrated in FIG. 1A, the PFC tail of the PF-protein sinks into the PFC reservoir. The test tubes are allowed to stand at room temperature for at least 12 hours to allow complete bonding of the PF-protein to the PFC reservoir and to allow the PFC to equilibrate with air. Excess PF-protein solution is then gently aspirated off.

Tensiometric measurements were made to determine the stability of the PF-protein at the PFC/aqueous interface. In one preferred embodiment, a du Noüy ring used to measure interfacial tension was immersed in a PFD reservoir. The PFD was then overlayed with PF-gelatin. After the PF-gelatin had bonded and equilibrated, water was slowly layered over the PF-gelatin. The results show that the interfacial tension at the PFD/PF-gelatin interface was approximately 32 dyne/cm, while the interfacial tension of PFD/water measured approximately 50 dynes/cm. The significantly lower interfacial tension indicates that the PF-gelatin bonded uniformly across the PFC surface.

Cell Growth

Culture Conditions and Growth on Different Substratums

In one preferred embodiment, once the PF-protein was bonded and equilibrated with the PFC reservoir, approximately $1-2\times10^5$ cells/cm$^2$ were seeded on the surface of the PF-protein/PFC interface using techniques well known in the art. In one preferred embodiment, a suspension of HeLa cells was trypsinized from a confluent stock culture and seeded at an initial cell density of $1.8\times10^5$ cells/cm$^2$ in Dulbecco's Modified Eagle's Medium (DMEM) supplemented with 10% Bovine Serum, glutamine (350 mg/liter), pyruvate (110 mg/liter), 30 nM N-2-Hydroxyethylpiperiazine-N-2'-2-ethane sulfonic acid (HEPES), penicillin (100 Units/ml), streptomycin (100 µg/ml) and 33 mM NaHCO$_3$. The cells quickly settled to the surface and adhered to the PF-protein surface. The tubes were incubated at 37.5° C. in an air-5% CO$_2$ incubator. They were replenished with fresh medium every 2 days during the first 3 to 5 days of culture, and more frequently after that to keep the pH between 7.2–7.4. For comparison, HeLa cells were also grown on PFD without gelatin, on PFD overlayed with gelatin that had not been perfluoroalkylated, and on conventional polystyrene tissue culture plates.

Figure 2:
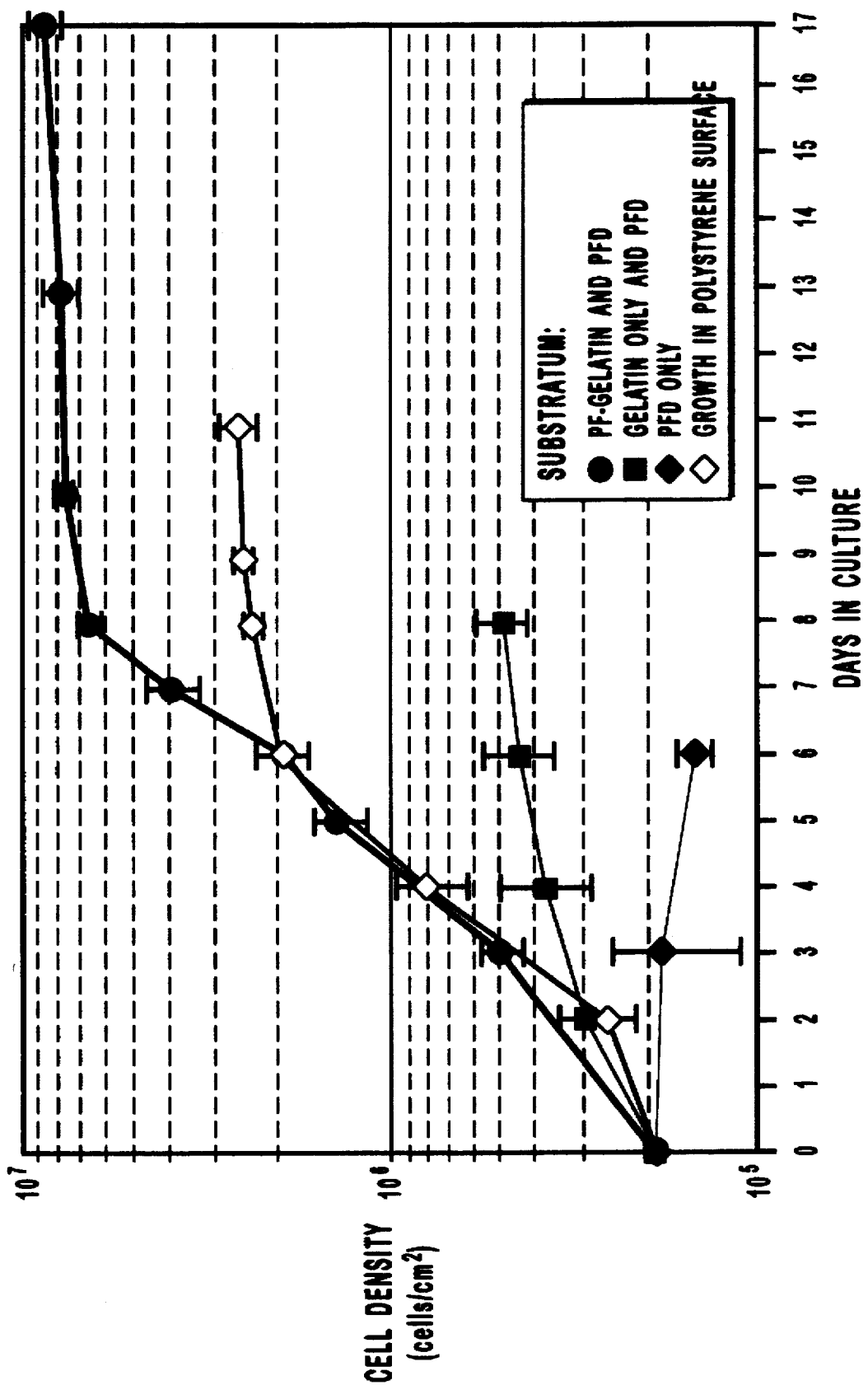
FIG. 2 is a graph illustrating HeLa cell growth (cells/cm$^2$) on different substratums. Black circles represent growth on perfluorodecalin treated with perfluoroalkylated gelatin. Black squares represent growth on perfluorodecalin treated with gelatin that had not been perfluoroalkylated. Black diamonds represent growth on untreated perfluorodecalin. Open diamonds represent growth on a conventional polystyrene surface.

A comparison of the growth rates on these different substratums is illustrated in FIG. 2. It will be appreciated that after a variable delay of 1–2 days (lag phase), the cells on the PF-gelatin surfaces grew at an exponential rate until day 8. Exponential rates of growth indicated that the cells in the culture were healthy and undergoing mitotic division. After this exponential phase, the growth acceleration declined although the overall cell density continued to increase for at least 17 days, reaching a final density of about $9\times10^6$ cells/cm$^2$. In comparison, cells did not grow at all when plated directly on PFD. In fact, the number had declined after 4 days and few cells survived. Cells inoculated on PFD covered only with nonperfluoroalkylated gelatin attained an exponential growth rate that was much lower than the PF-gelatin system. Again, inspection of the cultures indicated that most of the cells were aggregating around the rim of the test tube, probably adhering to and growing on the gelatin which had migrated to the walls of the polystyrene tubes. The final cell density in tubes with nonperfluoroalkylated gelatin was only about $4.8 \times 10^5$ cells/cm$^2$. These data demonstrate that perfluoroalkylation of the gelatin is essential for cell growth. Finally, FIG. 2 reveals the superiority of culturing cells on the substratum of the present invention over conventional polystyrene plates. Cells grown on polystyrene plates grew at log phase only until day 6. Moreover, cell density only reached a maximum of approximately $2.49 \times 10^6$ cells/cm$^2$.

It will be appreciated by one skilled in the art that numerous other cell types may be grown on the PF-protein/PFC substratum of the present invention. Examples include, hepatocytes, liver cells, cancer cells, nerve cells, heart cells. In addition, it will be appreciated that the present invention is particularly well suited for growing co-cultures which is hereby defined as simultaneously culturing multiple cell types. Finally, it will also be appreciated that in accordance with the prior art, the specific growth media, extracellular protein and incubation conditions may be altered to meet the needs of the particular cells being cultured.

Varying Volumes of PFC

Based on the premise that density-dependent inhibition results in part from inadequate oxygenation, decreasing the volume of the PFC reservoir should result in a concomitant decrease in cell density. To test this theory, in one preferred embodiment, a series of test tubes were set up with 0.25, 0.3 and 0.88 mls PFD. Since 0.3 mls of PFD did not cover the bottom of the tube, small glass beads (diameter 50–100 μm) were added to provide the same top surface area as in tubes with 0.88 mls. PFD has a very low surface tension so that the 0.3 mls permeated between the beads leaving a thin layer on top on which the PF-gelatin was bonded. A slightly smaller volume (0.25 mls) was also tested using specially designed flat bottom test tubes which were made to have the same cross sectional area.

Figure 3:
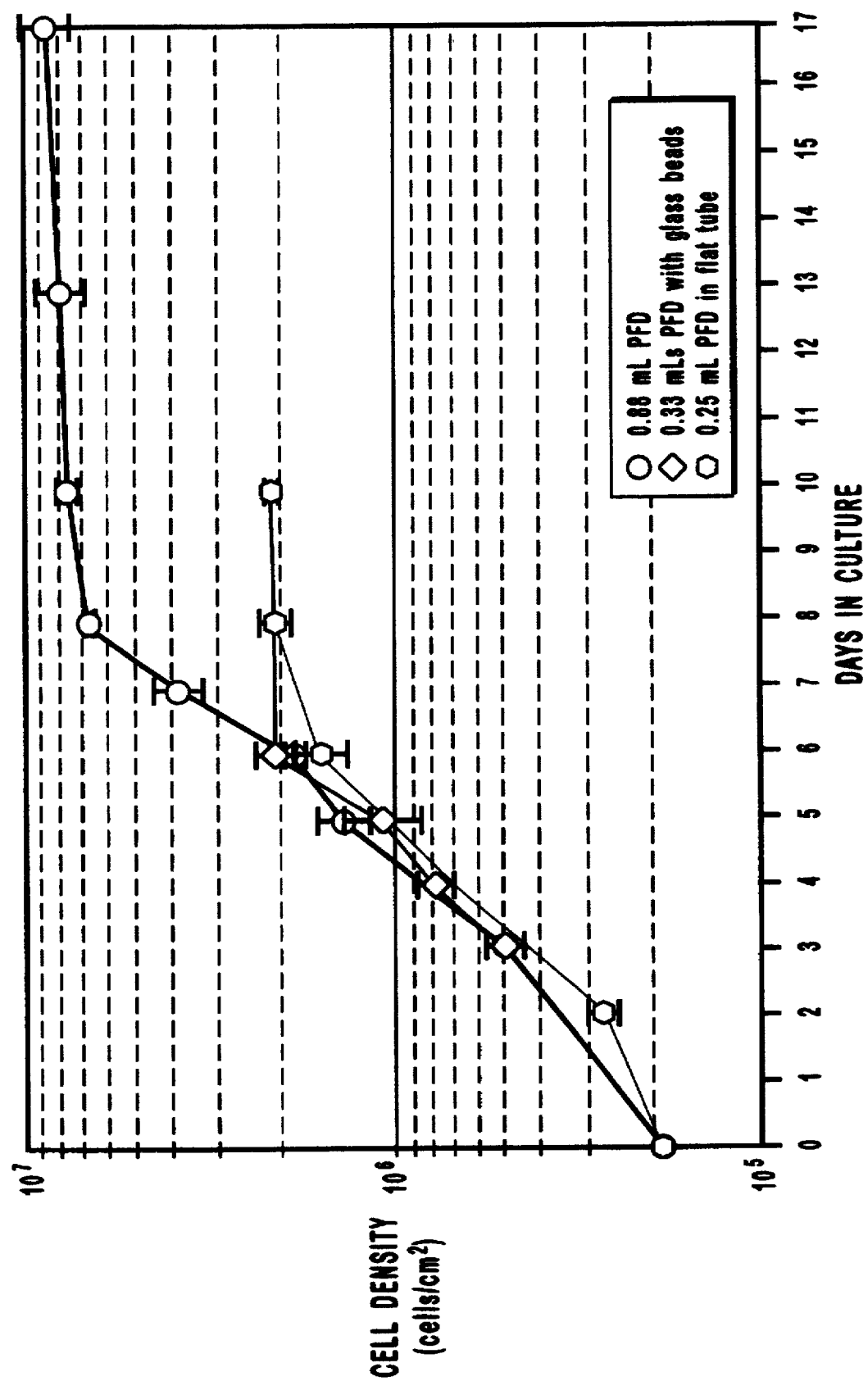
FIG. 3 is a graph illustrating HeLa cell growth (cells/cm$^2$) in test tubes containing varying amounts of perfluorodecalin.

It is seen in FIG. 3 that in tubes with 0.88 mls of PFD, cells continued to grow for 10 days reaching a final cell density of $8.8 \times 10^6$ cells/cm$^2$ as in the previous experiments. In contrast, in the tubes with only 0.3 mls and 0.25 mls PFD, both round and flat bottom, growth stopped at 10 days at a density of only $2.2 \times 10^6$ cells/cm$^2$. This finding suggests that the high cell densities reached using PF-gel/PFD substratums were not due to the state of the collagen. They are most reasonable ascribed to better oxygenation at the substratum due to diffusion from PFD. The findings also suggest that cells stopped growing in the polystyrene wells as a result of oxygen depletion at the polystyrene interface.

Open vs. Closed Reservoir PFC System

Figure 4:
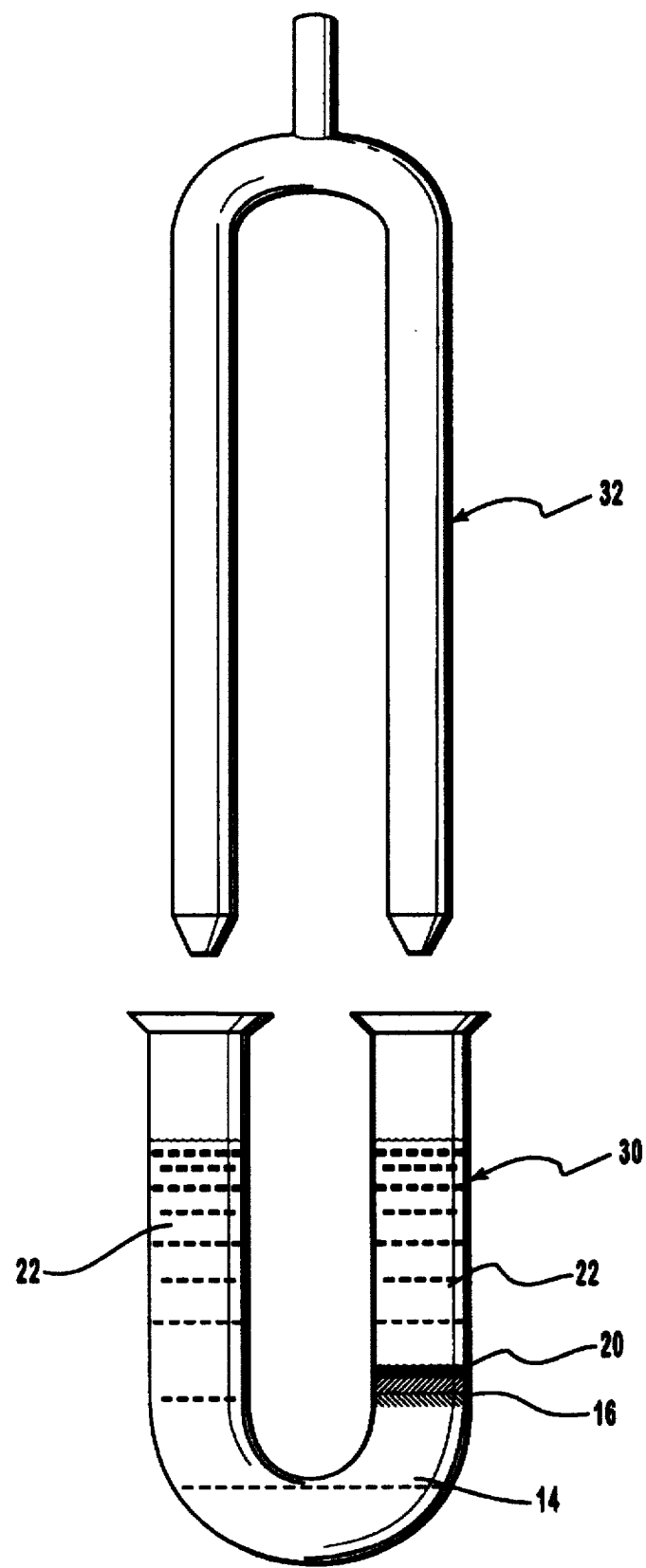
FIG. 4 is a cross sectional view of one embodiment of the present invention illustrating a U-shaped test tube used to culture HeLa cells. On one neck of the tube, HeLa cells are grown on a perfluoroalkylated-gelatin/perfluorodecalin substratum, while the opposite neck contains no cells and permits limited reoxygenation of the perfluorodecalin reservoir.

In order to study the effect of reoxygenation of the PFC reservoir, cell cultures grown in test tubes (closed system) were compared to cells cultured in a test tube which permitted the PFC reservoir to reoxygenate (open system). With reference to FIG. 4, in one preferred embodiment, cells were cultured in a U-shaped test tube 30. The PFC reservoir 14 was formed by adding 9 mls of PFD to the U-shaped test tube 30. To the surface of the PFC reservoir 14 (on only one arm of the U-shaped test tube 30) was bonded a PF-protein/PFC substratum 16 to which anchorage-dependent cells 20 could attach and grow. Finally, both arms of the U-shaped test tube 30 were filled with aqueous culture media 22. In all other respects both sides of the U-tube were treated identically. With continued reference to FIG. 4, in order not to disturb the cells during feeding, a tuning fork shaped pipet 32 was used to add and remove liquid from both sides of the U-shaped tube 30 simultaneously.

Figure 5:
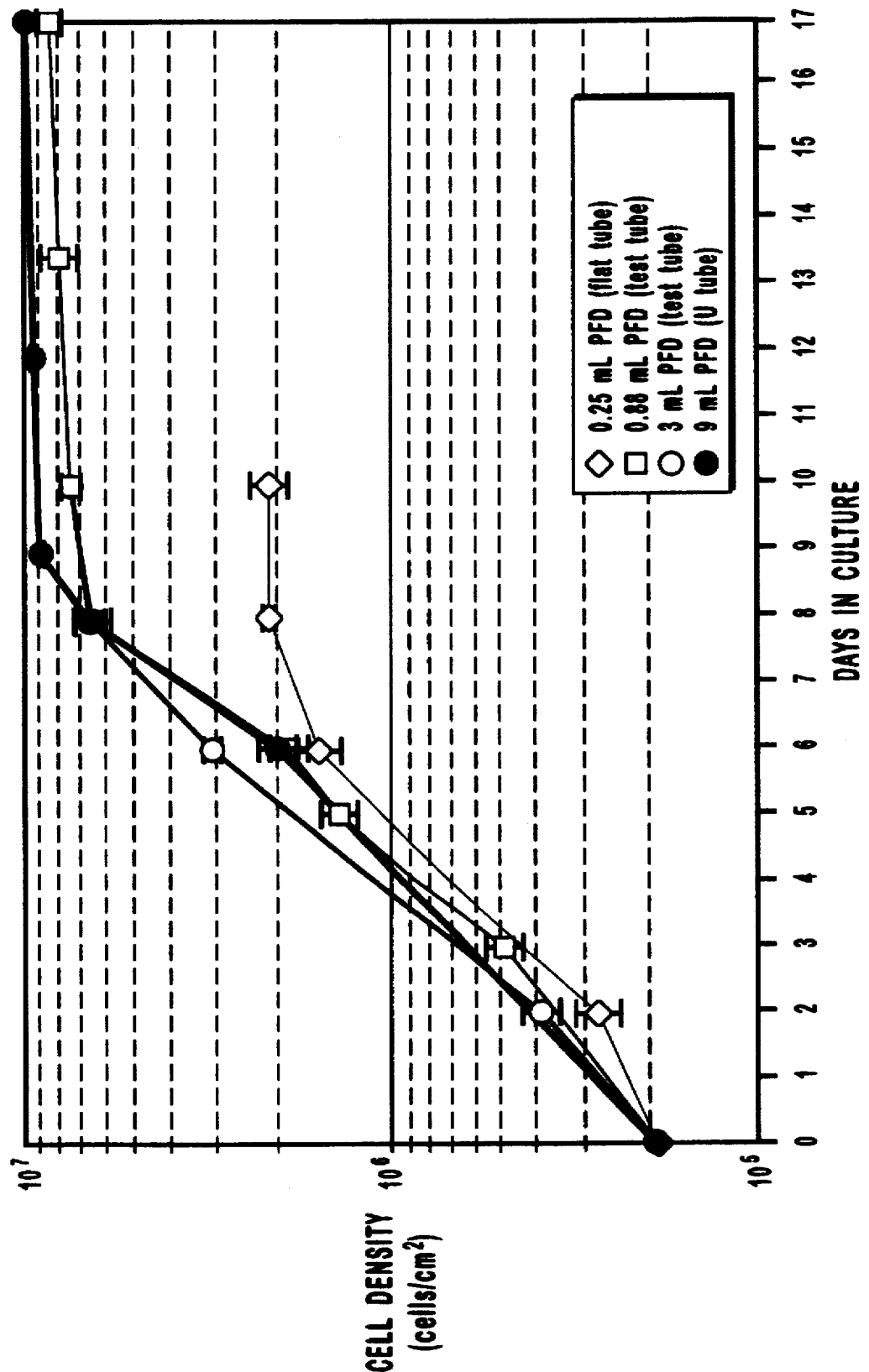
FIG. 5 is a graph illustrating HeLa cell growth (cells/cm$^2$) in test tubes containing varying amounts of perfluorodecalin versus HeLa cell growth in a U-shape test tube which permits some reoxygenation of the perfluorodecalin reservoir.

The results of culturing the cells in an opened versus a closed system are illustrated in FIG. 5. The growth rates for both curves are about the same. However, the exponential phase of growth in the U-tube lasted about 24 hours longer than the exponential growth of cells in the test tubes. Cells in the U-tube also were maintained at a higher cell density than those in the test tubes, reaching a density of $1.0 \times 10^7$ cells/cm$^2$ at day 17. The more prolonged exponential growth phase and the higher cell density that could be maintained are even more significant in view of the fact that the U-tube contained only 5 mls of growth medium whereas the test tubes had 11 mls. Also, the pH in the U-tube declined so rapidly that after 6 days they had to be replenished with growth medium every 5 hours. Even with this frequent replenishment, the pH could not be maintained above 7.2 which is below the optimal pH for HeLa growth.

Multilayer Formation

As discussed above, HeLa cells growing in U-tubes on a PF-gelatin/PFD substratum attained densities of about $1.0 \times 10^7$ cells/cm$^2$. In contrast, cells grown in conventional systems using polystyrene wells reached densities of only about $2.6 \times 10^6$ cells/cm$^2$. This suggested that with improved oxygenation cells were able to grow in layers on top of each other instead of being restricted to the "monolayer" obtained on solid surfaces.

To test this theory, a 15-day old culture from a U-tube was fixed, embedded, stained and sectioned using histological techniques well known in the art. Briefly, the cells were fixed with glutaraldehyde and dehydrated by soaking them in increasing concentrations of ethanol and finally in acetone. Fixed and dehydrated cells were then slowly raised to the top of the U-tube and embedded in glycol methacrylate and benzoyl peroxide. The block of embedded tissue was sectioned and stained with hematoxylin and eosin which stain the nuclei and the cytoplasms of the cells blue and pink, respectively.

Figure 6:
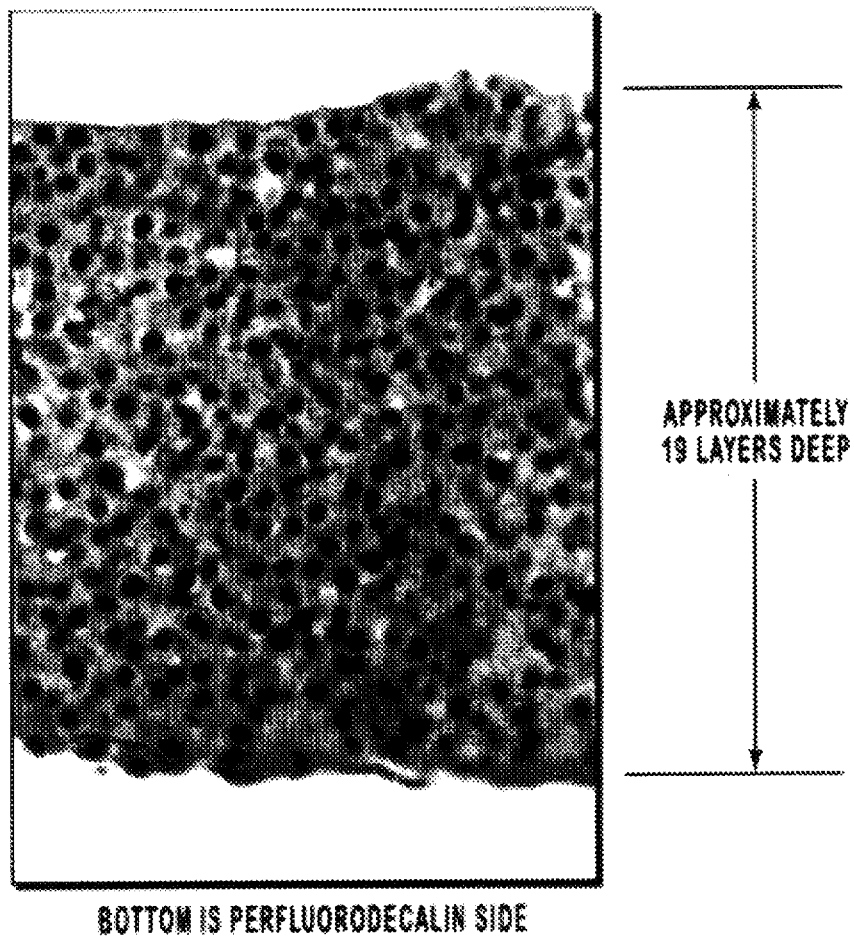
FIG. 6 is a photograph of a hematoxylin and eosin stained 3 micron vertical thin section of a 15-day old HeLa cell culture grown on a perfluoroalkylated-gelatin/perfluorodecalin substratum in the U-shaped test tube configuration. The dark stained areas are the nuclei. This photograph was taken with a green filter at 40× magnification.

A photomicrograph of a thin 3 micron vertical section of the embedded culture is shown in FIG. 6. Cells grew to form a tissue-like structure of more than 19 layers. It is also important that the bottom side of the layers adhering to the PF-gelatin is parallel with the upper surface. This strongly indicates that the architecture was indeed due to cells growing on top of each other to form many layers and not just due to a superficial aggregation of the cells. The section is also free of any necrotic areas as seen in spheroids. Most importantly, mitotic figures are observed deep in the section indicating that the level of oxygen needed for growth was maintained across the multilayers of cells.

EXAMPLES

The following examples are given to illustrate various embodiments which have been made with the present invention. It is to be understood that the following examples are not comprehensive or exhaustive of the many types of embodiments which can be prepared in accordance with the present invention.

Example 1

Purification of Gelatin

In one experiment, the protein used to construct the PF-protein/PFC substratum of the present invention was gelatin. Before use, the gelatin was purified as follows. Commercial gelatin (Sigma, G-2500, Type A, 300 Bloom)

was fractionated using 50% v/v of isopropyl alcohol (IPA, EM Sciences, PX 1835-1). All equipment used was autoclaved and all solutions sterilized by filtration through a sterilized 0.2 μm filter. Two autoclaved bottles were used to store 60 mls IPA and 60 mls 50% IPA diluted with deionized water. Both bottles were stored in a freezer. Gelatin (10 mg/mls) was dissolved in 50 mls of water by stirring at room temperature. Fifty milliliters of cold IPA were added to the 50 mls of the gelatin solution. This bottle was stored in the freezer for at least 24 hours. The precipitate was collected by centrifugation at 4000 G at 5° C. for 15 minutes and the supernatant removed. Fifty milliliters of cold 50% IPA solution were added with gentle mixing and stored in the freezer for at least 24 hours and the solution was again centrifuged and the supernatant discarded. The washed precipitated gelatin was resuspended in 10 mls of 0.1M sodium phosphate buffer solution, pH 8.5, and stored at 4° C.

Example 2

Preparation and Assay of Perfluoroalkylated Gelatin

The purified gelatin from Example 1 was then perfluoroalkylated. The perfluoroalkylating agent (PF-agent), perfluorooctylpropyl isocyanate ($C_8F_{17}(CH_2)_3NCO$), was donated by du Pont Co. The isocyanate group reacts with water and therefore, the perfluoroalkylation was done in a moisture free atmosphere. A glove box was flushed with nitrogen which had been passed through a canister of Drierite (W. A. Hammond Drierite Co.), and then through a 0.2 μm filter to ensure a moisture free sterile atmosphere. Ten microliters of the PF-agent were added to 40 microliters HPLC-grade acetonitrile (Aldrich, 27071-7) and vortexed for 5 seconds. Any unused PF-agent solution was returned immediately to storage. The 50 microliters PF-agent/ acetonitrile mixture was then added to 9 mls of purified gelatin and stirred for 2 hours.

The number of amino groups of the gelatin that were perfluoroalkylated was determined by a fluorescamine assay. Fluorescamine conjugates readily with free amino groups. A calibration curve was made using glycine. A standard solution of 80 μg/mls glycine (Sigma, G-7126) was prepared in a 0.1M sodium phosphate buffer solution, pH 8.5. A stock solution of fluorescamine (0.3 mg/ml) was made in OmniSolv acetone (EM Science, AX0116-3). Assay tubes were set up for calibrating a range of glycine concentrations from 0 to 8 μg/ml. After adding the fluorescamine, the tubes were vortexed and allowed to stand for 10 minutes. The fluorescence was measured using a Model A-4 System Filter Fluorometer (Optical Technology Devices, Inc.) at an excitation wavelength of 350 nm. The concentration of amino groups versus fluorescence was fit by linear regression.

The gelatin solutions were assayed in the same way. The fluorescence value obtained on an assay of the native gelatin indicated the total number of amino groups available for perfluoroalkylation. The fluorescence of PF-gelatin assayed at the same concentration indicated the relative number of amino groups which had been perfluoroalkylated. The fraction of reacted groups is calculated as follows:

$$\gamma = 1 - \frac{\text{Conc. of amino groups in } PF\text{-gelatin}}{\text{Conc. of amino groups in gelatin}}$$

where γ is the ratio of reacted amino groups in PF-gelatin and conc. is the concentration of amino groups obtained from the calibration curve.

Example 3

Bonding of the Perfluoroalkylated Gelatin to PFD

The perfluoroalkylated gelatin of Example 2 was then bonded to the PFC reservoir as follows. Seven sterile 15 mls tissue culture polystyrene test tubes (Falcon, 3033) were used for each experiment. Perfluorodecalin (0.88 ml) was added to each test tube. This was sufficient to cover the round bottom of the test tube providing a cross sectional surface area of 1.33 $cm^2$ as a substratum for growth. PF-gelatin (0.5 ml) was added to each tube to completely cover the top surface of the PFD reservoir. The tubes were allowed to stand at room temperature for at least 12 hours to allow complete bonding of PF-gelatin to the PFD reservoir and to allow the PFD to equilibrate with air. Excess PF-gelatin solution was then gently aspirated off.

Example 4

Tensiometer Experiment

Once the PF-protein had bonded to the PFC reservoir, tensiometric measurements were made to determine the stability of the PF-protein at the aqueous/PFC interface. Twenty milliliters PFD were added to an empty beaker. A du Noüy ring, a platinum ring used to measure interfacial tension, was immersed completely the PFD. Five milliliters of perfluoroalkylated gelatin (10 mg/mls) were then added and the two phases were allowed to equilibrate for 12 hours. Next, 10 mls of water were slowly added. The interfacial tension of the PFD/aqueous and aqueous/air interfaces were measured at certain time intervals after water being adding. The results indicate that the PF-gelatin/PFD interfacial tension was about 32 dyne/cm, while the PFD/water interfacial tension was about 50 dyne/cm. The lower interfacial tension at the PF-gel/PFD interface indicates that a very stable surface had formed. By contrast, the interfacial tension of the water/PF-Gelatin interface approached the interfacial tension for water/air surfaces.

Example 5

Culturing HeLa Cells on PF-gelatin/PFD Substratum

The PF-protein/PFC substratum of Example 3 was then seeded with anchorage-dependent HeLa cells. Specifically, a suspension of HeLa cells was trypsinized from a confluent stock culture and diluted into DMEM containing 33 mM bicarbonate and 10% bovine calf serum to give about $2.2 \times 10^4$ cells/mls. After flushing with carbon dioxide, 11 mls were added to PF-gel/PFD containing test tubes (diameter 1.33 $cm^2$) giving an initial cell density of $1.8 \times 10^5$ cells/$cm^2$. Cells quickly settled to the surface and adhered to the PF-gel/PFD substratum. The tubes were incubated at 37.5° C. in an air-5% $CO_2$ incubator. They were replenished with fresh medium every 2 days during the first 3 to 5 days of culture, and more frequently after that to keep the pH between 7.2–7.4. One tube was withdrawn after 2, 4, 6, 8, 10, 13, and 17 days of incubation. The medium was removed. The cell layer rinsed with PBS and then trypsinized for cell counts. Growth was expressed as an increase in cell density, e.g., cells/$cm^2$ as determined by cell counts.

Example 6

Culture Conditions

HeLa cells of Example 5 were cultured by methods well known in the art. Briefly, HeLa cells were grown in Dulbecco's Modified Eagle's Medium (DMEM) (Sigma Chemical Co. #D-7777) containing 10%. Bovine calf serum (Hyclone Laboratories #A-2111), 1% Penicillinstreptomycin from a 5000 units/mls penicillin and 5 mg/mls streptomycin stock (Sigma Chemical Co. #P-0906) dissolved in sterile DMEM, 2.5% of a 1M solution of N-2-Hydroxyethylpiperiazine-N-2'-2-ethanesulfonic acid (HEPES), and 3.3% of a 1M solution of sodium bicarbonate. Cultures were incubated at 37.5°±0.2° C. in an air-5% $CO_2$ incubator. Cell prepared from a frozen stock were passed at least once before being used in experiments.

Example 7

Cells Form Multilayers in the PF-Gelatin/PFD System

Cells were grown as described in Example 6 except that a U-tube (Fisher, 09-235A, 1.3 cm diameter and about 1.33 $cm^2$ surface area) containing 9 mls of PFD was used. After 15-days in culture, the cells were fixed, embedded, stained and sectioned as follows. The medium in the U-tube was removed using the double barreled pipette and the U-tube was rinsed with phosphate buffered saline to remove non-adhering cells. The layer was fixed by two 10-minute treatments with glutaraldehyde. This stabilizes cell structure and prevents autolysis. The cells were then dehydrated for 20 minute each in 70%, 80% and 95% ethanol and finally 100% acetone.

The fixed and dehydrated layer of cells was then slowly raised to the top of the U-tube so that it could be treated for embedding. The cell layer was then removed slowly using a syringe pump (Orion Research Inc., Model 355) to pump PFD into the other arm of the tube that did not have cells. The PFD was pumped in at a rate of 3 mls/min.

After the layer was raised to the top, it was floated off into a small vessel where it could be embedded. This was done in two steps. Briefly, 5 mls of Solution A containing glycol methacrylate (GMA) monomer was added. The preparation was allowed to stand 2 hours in order for the monomer to infiltrate into the cell layers. This procedure was repeated by removing old Solution A and adding fresh Solution A. Then Solution A was removed and an embedding solution was added for about an hour. This solution consisted of a mixture of 5 mls Solution A and 0.4 ml Solution B containing benzoyl peroxide, which catalyzes the polymerization of the monomers and hardens the layer.

The block of embedded tissue was sectioned and stained with hematoxylin and eosin. Hematoxylin was used to stain the nucleus of a cell blue and eosin was used to stain the cytoplasm pink. A photomicrograph of a thin 3 micron vertical section of the embedded culture is shown in FIG. 6.

SUMMARY

In summary, growth of cells on PF-protein/PFC substratums can support sustained growth of cells in a three-dimensional tissue-like structure. Growth in multilayers is believed to be primarily due to three factors. First, high concentration of oxygen is delivered to the cells by PFCs. Second, the oxygen is delivered to the cells from a PFC reservoir beneath the cells and also from the aqueous medium above the cells. This minimizes the amount of oxygen coming from the aqueous media which contains metals and metabolites which produce free radicals when reacted with molecular oxygen. Finally, the cells are not in direct contact with the PFC which has been shown to affect the biological activity of some cells in culture.

What is claimed and desired to be secured by United States Letters Patent is:

1. A method for the attachment and growth of cells comprising the steps of:
   a. contacting a surface with a perfluorocarbon;
   b. bonding a perfluoroalkylated protein to the perfluorocarbon such that a perfluoroalkylated/perfluorocarbon substratum is formed;
   c. adding aqueous growth media; and
   d. contacting the perfluoroalkylated/perfluorocarbon substratum with cells.

2. The method of attaching and growing cells of claim 1 wherein the perfluorocarbon is selected from the group consisting of perfluorodecalin, perfluorotributylamine and perfluorobutyltetrahydrofuran.

3. The method of attaching and growing cells of claim 1 wherein the perfluoroalkylated protein has a perfluorocarbon tail, and wherein the perfluorocarbon tail is perfluorooctylpropyl.

4. The method of attaching and growing cells of claim 1 wherein the perfluoroalkylated protein is selected from the group consisting of gelatins, collagens, fibronectins, laminins and elastins.

5. The method of attaching and growing cells of claim 1 wherein the cells are eukaryotic cells.

6. The method of attaching and growing cells of claim 5 wherein the cells are co-cultured.

7. The method of attaching and growing cells of claim 1 wherein the eukaryotic cells are selected from the group consisting of HeLa cells, hepatocytes, liver cells, cancer cells, bone marrow cells, nerve cells, heart cells and co-cultures of the above.

8. The method of attaching and growing cells of claim 6 wherein the cells grow to form multiple cell layers following contact with the perfluoroalkylated/perfluorocarbon substratum.

9. The method of attaching and growing cells of claim 1 wherein the aqueous growth media is not in direct contact with the perfluorocarbon.

10. The method of attaching and growing cells of claim 1 wherein the surface contacted with perfluorocarbon is a closed system.

11. The method of attaching and growing cells of claim 1 wherein the surface contacted with perfluorocarbon is an open system.

12. A method for the attachment and growth of cells comprising the steps of:
   a. contacting a surface with a perfluorocarbon;
   b. perfluoroalkylating a protein;
   c. bonding the perfluoroalkylated protein to the perfluorocarbon such that a perfluoroalkylated/perfluorocarbon substratum is formed;
   d. contacting the substratum with aqueous growth media; and
   e. contacting the perfluoroalkylated/perfluorocarbon substratum with at least one anchorage-dependent eukaryotic cells and allowing the anchorage-dependent eukaryotic cells to grow.

13. The method of attaching and growing cells of claim 12 wherein the perfluorocarbon is selected from the group consisting of perfluorodecalin, perfluorotributylamine and perfluorobutyltetrahydrofuran.

14. The method of attaching and growing cells of claim 12 wherein the protein is selected from the group consisting of gelatins, collagens, fibronectins, laminins and elastins.

15. The method of attaching and growing cells of claim 12 wherein the eukaryotic cells are selected from the group consisting of HeLa cells, hepatocytes, liver cells, cancer cells, nerve cells, heart cells and co-cultures of the above.

16. The method of attaching and growing cells of claim 12 wherein the cells form multiple cell layers.

17. The method of attaching and growing cells of claim 12 wherein the aqueous growth media is not in direct contact with the perfluorocarbon.

18. The method of attaching and growing cells of claim 12 wherein the surface contacted with perfluorocarbon is a closed system.

19. The method of attaching and growing cells of claim 12 wherein the surface contacted with perfluorocarbon is an open system.

* * * * *

UNITED STATES PATENT AND TRADEMARK OFFICE
CERTIFICATE OF CORRECTION

PATENT NO. : 5,702,949
DATED : December 30, 1997
INVENTOR(S) : Edward M. Trujillo, Catherine Rappaport It is certified that error appears in the above-identified patent and that said Letters Patent is hereby corrected as shown below:

Please insert the following at Column 1 beginning after the title:

"This invention was made with government support under NSF Grant No. BCS-9011647. The government has certain rights in the invention."

Signed and Sealed this

Eighth Day of September, 1998

Attest:

BRUCE LEHMAN

Attesting Officer     Commissioner of Patents and Trademarks